United States Patent [19]

Burton

[11] 4,067,342
[45] Jan. 10, 1978

[54] TAPE ELECTRODE

[75] Inventor: Charles V. Burton, Wayzata, Minn.

[73] Assignee: Medtronic, Inc., Minneapolis, Minn.

[21] Appl. No.: 674,176

[22] Filed: Apr. 6, 1976

[51] Int. Cl.² .............................................. A61N 1/04
[52] U.S. Cl. ................................................... 128/418
[58] Field of Search ............... 128/418, 404, 416, 417, 128/2.06 E, 2.1 E, DIG. 9

[56] References Cited

U.S. PATENT DOCUMENTS

| | | | |
|---|---|---|---|
| 3,426,746 | 2/1969 | Seamans, Jr. | 128/2.06 E |
| 3,543,761 | 12/1970 | Bradley | 128/418 X |
| 3,547,105 | 12/1970 | Paine | 128/2.06 E |
| 3,565,059 | 2/1971 | Hauser | 128/2.06 E |
| 3,607,788 | 9/1971 | Adolph | 128/418 X |
| 3,721,246 | 3/1973 | Landis | 128/404 |
| 3,911,906 | 10/1975 | Reinhold, Jr. | 128/2.06 E |
| 3,964,470 | 6/1976 | Trombley | 128/2.1 E |

FOREIGN PATENT DOCUMENTS 2,521,697  12/1975  Germany ........................ 128/2.06 E Primary Examiner—Robert W. Michell
Assistant Examiner—Lee S. Cohen
Attorney, Agent, or Firm—Schroeder, Siegfried, Ryan, Vidas & Steffey

[57] ABSTRACT

A tape electrode usable for the transmission of electrical signals into the human body through the skin. The electrode is flexible in construction so that it may be applied to the skin to secure good electrical contact therewith and remain in place for extended periods despite movement, perspiration and the presence of water on the skin surface. The tape construction includes a surface of a conductive material combined with an adhesive on one surface and the conductive material with a magnetic powder on the second surface together with a coupler through a permanent magnet or magnetic substance to which a lead wire is connected to effect electrical connection through the conductive material in the adhesive and retain the lead wire in position through the magnetic attraction of the permanent magnet to the magnetic material.

11 Claims, 7 Drawing Figures

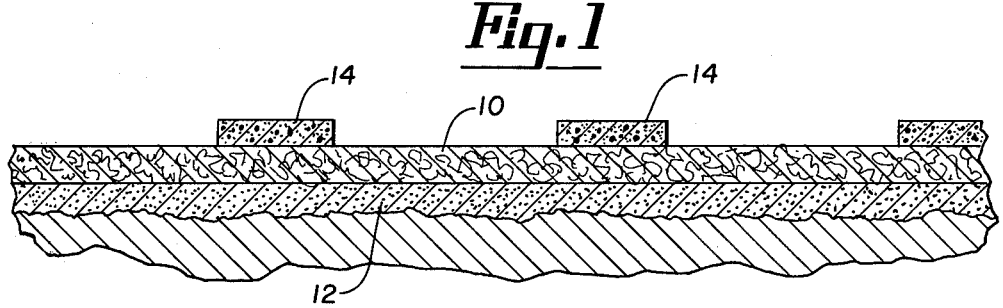
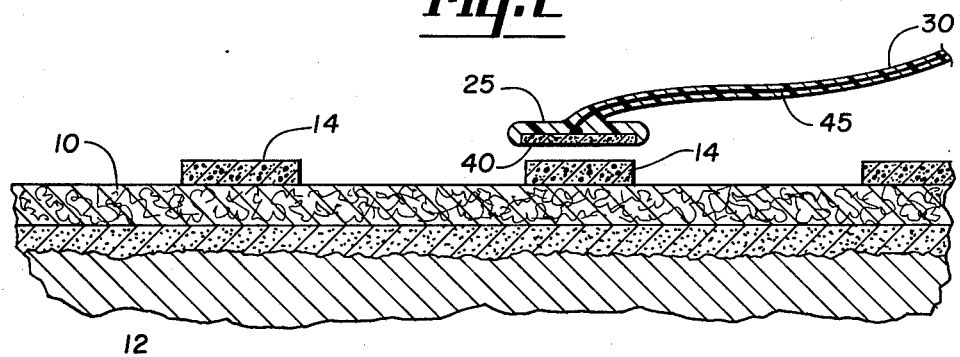
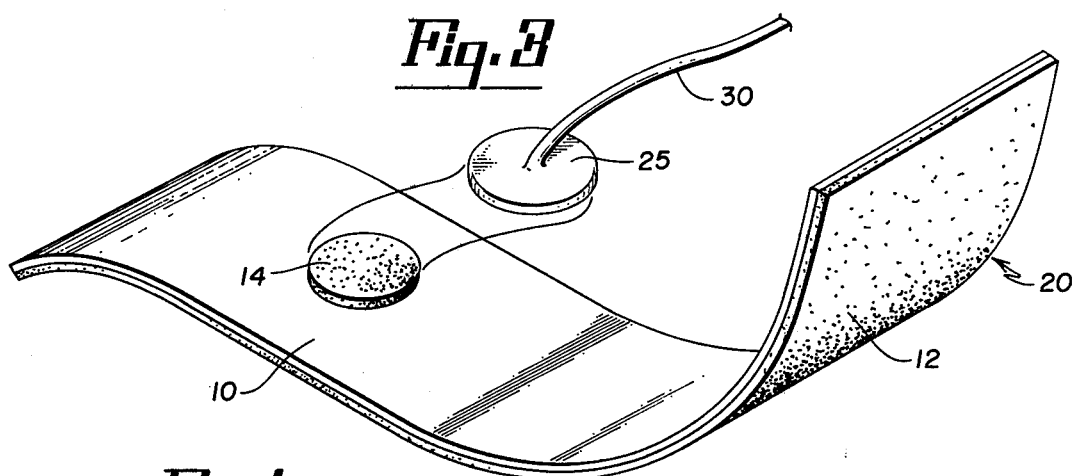
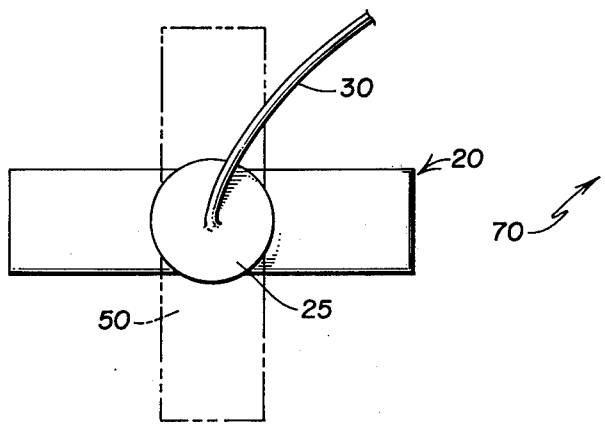
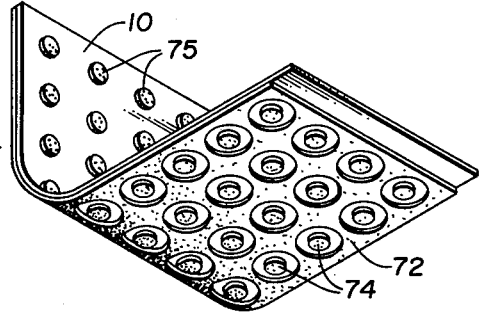

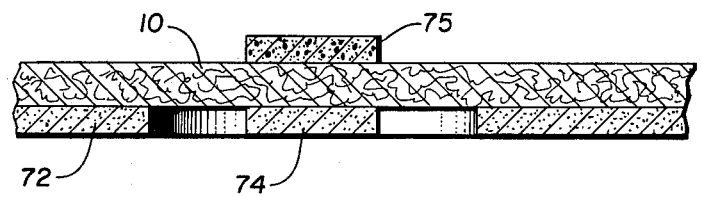
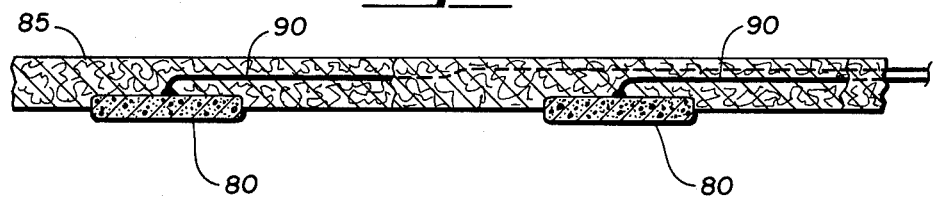

TAPE ELECTRODE

The present invention is directed to electrodes for application to the outer layer of the skin of a human body and more particularly to an improved electrode of this type taking the form of disposable solvent-activated tape together with an improved coupler for applying electrical current thereto.

The present application is an improvement over my co-pending application Ser. No. 567,612 filed Apr. 14, 1975, now U.S. Pat. No. 4,008,721, entitled TAPE ELECTRODE FOR TRANSMITTING ELECTRICAL SIGNALS THROUGH THE SKIN. This type of an electrode is basically used as a transmission electrode for passing quantities of electrical energy into the human body greater than normally transmitted by monitoring electrodes. The latter, because of the low current levels involved, rely on conductive jelly for providing electrical contact between the electrode and the skin and are widely used. The present electrode has been designed to apply current over a large area of the skin in the form of a disposable tape which may be readily applied to and removed from the skin. This type of electrode must be one which is capable of being used by a lay person so that no special skills are involved in its application or removal. More importantly, the improved electrode must be capable of conforming to the normal curvature of the body and being left on the skin for significant periods of time for various types of medical application such as pattern recognition.

In the present invention, a tape electrode, such as is shown in my co-pending application, is coupled with a magnetic and electrically conductive material on the same or opposite side from the conductive backing permitting the attachment of a lead wire thereto through the use of a permanent magnet or magnetic substance formed about the lead wire to effectively and positively connect the electrical circuit to the tape electrode and insure that it will not be displaced therefrom during usage. As in my co-pending application, the electrode, in order to be somewhat permanently fixed to the skin of a subject and tolerated by the subject must have characteristics which strongly discourage the growth of the pathologic microorganisms between the regions of the electrode and the skin layers. Similarly, because of the relative high density of power transmission into the skin of the subject, the conductivity of the electrode must be high enough to distribute the current load across the relatively broad area of the skin preventing hot spots that might burn the skin of the subject. Further, the materials involved must be non-allergenic to the skin of a great majority of the patients and, since it is disposable, the electrode must be relatively low in cost.

Because of the difficulty in connecting an electrical conductor to the tape type electrode and to insure uniformity of conductivity and permanency of contact while in use, the present invention is directed to a modification of the tape of my prior application to provide for a conductive magnetic surface thereof to which insulated lead conductors of a magnetic variety may be connected to the tape. This improved conductive tape with the localized magnetic backing permits the coupling in a reusable overlay or lead-in and further, permits the tape to be formed in a plurality of circuits which would provide a cutaneous type coupling system capable of allowing pattern recognition by the patient. This system would allow for high fidelity pattern recognition by providing for a number of contact spots on the skin with a single sheet of tape. In addition to the display of functional prosthesis systems, such as visual and auditory, the display can be used for many other transducer functions such as bio-feedback. Thus, the present invention, the improved conductive tape may add one or more conductive surfaces on one side of the tape substrate with localized coating of conductive and magnetic material on the other side of the tape to enable a lead wire to be coupled thereto and held in position thereon through the use of a permanent magnet or magnetic substance with a plurality of such lead-ins in the overlay for the display system. The tape system permits the "breathing" of same to allow escape of normal amounts of perspiration from the skin of the subject. The adhesive layer, which is normally dry is initially activated by a suitable solvent and reactivated at any time by a suitable solvent and reapplied through the same process.

Therefore, the present invention provides an improved solvent activated conductive tape with a magnetic coupler system.

Another object of this invention is to provide an improved conductive tape which is disposable and which may be used with a magnetic type overlay for coupling a lead or leads to the tape.

A further object of the invention is to provide an improved tape with a plurality of contact areas allowing for pattern recognition.

A still further object of this invention is to provide a tape of this type which is relatively low in cost and is easy to use.

These and other objects of this invention will become apparent from the reading of the attached description together with the drawings wherein:

FIG. 1 is a side cross-sectional view of the tape form electrode in accord with the present invention;

FIG. 2 is a side cross-sectional view of a tape form electrode with a connector overlay associated therewith;

FIG. 3 is a perspective view of the tape with a coupler overlay apart from the same;

FIG. 4 is a plan view of the conductive tape with the lead in overlay coupled thereto showing an application of the same;

FIG. 5 is a perspective view of a modified form of the improved conductor tape;

FIG. 6 is a side cross sectional view of the tape of FIG. 5 with parts broken away;

FIG. 7 is a plan view of an overlay sheet providing electrical connections to the tape of FIG. 5.

In FIG. 1 there is shown in enlarged cross-sectional view, for the purpose of illustration, my improved tape electrode made in accord with the present invention. This tape electrode includes a backing material or substrate 10 onto which the active materials forming the electrode are applied. The substrate or backing material is preferably a thin, flexible, porous cloth-like material through which water vapor or water in liquid form may permeate. This characteristic is an essential requirement to permit moisture which may be generated on the surface of the skin of the patient to exit from the skin without lifting or altering the adhesion of the tape electrodes through prolonged usage. The material similarly is not water soluable and it has been found that a nonwoven brand fiber material is satisfactory for this purpose.

The tape substrate 10 has positioned on one side thereof, a layer 12 of an electrically conductive material. The latter is a combination of the adhesive material, such as an acrylic polymer adhesive, into which has been blended a quantity of silver metal to make the adhesive layer conductive. The quantity of silver that is incorporated into the layer may be varied within relatively broad limits and for the sake of economy, would be sufficient to provide in a good conductive path therethrough and yet be low enough to blend well with the adhesive and reduce the cost of the same. The acrylic polymer may be of the types sold by National Star Company under their designation Resin-30-1289 which is a vinyl acrylic polymer in an organic solvent. The silver powder is a finely divided silver metal which may be obtained from Handy and Harmon under their designation Silfake 135. As an example of the blend of proportions thereof for producing the adhesive conductive layer 12, it has been found that approximately 1000 grams of silver may be blended with 300 grams of copolymer material to make the coating. Similarly, the coating 12 may be preceded on the back of the substrate by a layer of the adhesive only, the adhesive being chosen because it is relatively permeable to moisture and will permit the exit of any perspiration materials which is generated by the skin under the normal usage. The layer of adhesive only, if used, would be just thick enough to provide the sealing function on the surface of the substrate and would be as little as one mil thickness. Increasing the amounts of silver in the mixture would reduce the volume resistivity of the coating 12 but would result in increased costs per unit of the electrode. Similarly, reducing the volume of the silver increases the volume resistivity of the same. It has been found that the volume resistivity of approximately one ohm centimeter is satisfactory for normal purposes. The combined acrylic polymer and silver coating applied to the substrate is relatively non-tacky enabling ready rolling and storage of the tape material. It may be readily fluidized or activated, however, by suitable solvent such as toluene and acetone. Such a solvent readily evaporates to leave a finished material tacky for usage. The thickness of the layer of electrically conductive surface is less than 5 mils thickness and preferably from 2 to 3 mils thickness.

The completed conductive tape, which is generally indicated as at 20, includes not only the conductive layer 12 on the substrate 10, but localized coatings 14 of the combination of the conductive coating with magnetic powders mixed therein. The addition of the magnetic powder, such as samarium cobalt, to the conductive coating of silver and the acrylic polymer makes this coating magnetic as well as electrically conductive. Thus, as will be seen in FIGS. 1 and 2, localized spot on the opposite surface of the tape substrate 10 of the magnetic and conductive coating are provided to facilitate the connecting of an electric conductor of the tape as will be hereinafter noted. As shown in FIGS. 1, 2, and 3, the addition of the magnetic coating or spots on the back of the tape is such that the adhesive in the conductive magnetic mixture will adhere to the substrate and may be activated by acetone solvent. Since the tape substrate is normally now conductive, the activation of the adhesive in the mixture on either side of the tape substrate will carry conductive particles in the layers 12 and 14 into mutual contact through the substrate to provide a bridging path or paths through the substrate. As the coupler to connect the lead wire, indicated at 30, to the conductive coating, thin, plate-like permanent magnets of a samarium cobalt material or other magnetic substance such as indicated at 40, are used and will have the lead wire connected thereto and shielded therefrom by a suitable shielding material 45. By bringing the permanent magnets or other magnetic substances with the lead wire attached thereto into contact with the localized coating or coatings on the back of the tape after the activating solvent is applied, electrical connection from the lead wire is made through the conductive material of the spot coating and through the tape substrate to the conductive coating. The connection of the lead wire to the tape may require only a single magnet and lead wire and the tape will normally provide a number of coating surfaces to which a lead connection may be connected for ease in connection. The completed tape may be made in various lengths and widths and would preferably be placed in a liner of a silicone or a polyurethane coated paper as protection to the coated surface until it is desired to actually use the section of the tape as an electrode. When the tape is to be used on the skin of a human, it can be attached thereto through the application of a solvent and may be readily tacky to make a good coupling on the skin surface. At this point, one or more of the couplers with lead wires may be applied to suitable coating spots on the back of the tape to provide the electrical connection thereto.

In FIG. 4, it will be seen that the tape 20 with the coupler 25 formed by the magnet and insulated lead wire 30 may additionally be held in position on the surface of the tape and held to the skin of the patient by means of a covering of non-allergic tape, such as is indicated at 50 in phantom.

In FIGS. 5 and 6, there is shown another embodiment of the tape which is particularly adaptable for a cutaneous display system. Thus, the conductive tape which is now indicated at 70 employs the same tape substrate 10 with the conductive coating applied to one surface thereto. In this embodiment, the conductive coating is applied as a general overall background 72 having a plurality of isolated spots of conductive coating 74 separated from the background by voids or non-conductivity surfaces. Thus, in the drawings, it will appear that the conductive coatings 74 which are made of the same material as the previous embodiment and applied to the substrate in the same manner, are isolated by annular areas or surfaces in which the conductive coating is absent and the general background is completed with a conductive layer 72. On the opposite side of the substrate, the combination of the conductive coating with the magnetic powder or particles 75 is positioned on the substrate in direct alignment with and opposite to the isolated conductive surfaces 74 providing a series of dots on the opposite side of the substrate corresponding with the isolated conductive surfaces 74 on the active side. Such a tape may be made disposable and reusable overlay consisting of a plurality of magnets 80 with lead wires attached thereto will supply connections to the tape. Thus, as will be seen in FIG. 7, there is attached to an overlay sheet 85, a plurality of magnets 80 each magnet having a lead conductor 90 connected thereto and shielded in such a manner such as to isolate each conductor from one another so as to provide the separate electrical connections to the spots 74. The overlay sheet may be made of a relatively flexible non-conductive material which flexes and conforms to the configurations of the tape on the skin. The magnet or magnetic substance and lead wires are attached to any adhesive which is moisture permeable and non-allergenic to the skin. The disposable portion or tape 70 as shown in FIG. 5, will provide a bi-polar electrode with dots representing one pole and the background representing a second pole with the dots being separated by a space from the background. On the backside of the tape, the dots of magnetic conductive coating indicate the areas of magnetic contact for the overlay sheet with the magnets thereon and with the separate conductors therein. The edges of the sheet will serve as a second contact to complete the electrical circuit. This will provide a display system whose fidelity will be proportional to the number of contact spots on the skin. Such a display system could be used for a visual or auditory transducer type of display for functional prothesis systems display of other transduced sensory modalities and could be used in biofeedback transducer function. The tape in this embodiment, as in the preferred previous embodiment, could be applied to the skin of the patient and left for extended periods of time. In the present invention, the magnetic surface on the tape provides a means for effectively coupling a lead wire thereto in the circuit through the conductive material of the tape. As indicated in the embodiments 5, 6, and 7, a plurality of circuits may be effected in the same manner in a single section of tape. The use of the magnetic coupler insures for positive electrical connection which will not be disturbed during usage and will be compatible with use on the patient.

Therefore, in considering this invention, it should be remembered that the present disclosure is illustrative only and the scope of the invention should be determined by the appended claims.

What I claim is:

1. A solvent activated conductive dry tape electrode for prolonged adhesion to the epidermal layer of the skin of a human which is readily activated and adherable with the application of a non-aqueous solvent comprising, a highly porous tape substrate, a conductive coating positioned on one surface of the substrate, said coating including a mixture of skin compatible metal particles blended into a water insoluble low tack adhesive matrix in an amount sufficient to supply electrical continuity between the metal particles with said adhesive matrix being non-toxic and non-irritating and including a non-allergenic polymer that is at least partially soluble in a volatile organic solvent, the adhesive matrix coating having a thickness such as to permit permeation of a water vapor generated on the surface of the skin through the coating layer and tape substrate, and a further coating including a mixture of said conductive coating and a magnetic material in which the conductive coating has the water insoluble adhesive matrix and metal particles to provide the electrical continuity between the particles and with the magnetic material being mixed in amounts sufficient to provide magnetic continuity between the magnetic particles, said further coating being applied to one surface of the substrate and separated from the conductive coating in a position to allow electrical continuity to exist between said coatings when the electrode is activated.

2. The conductive tape of claim 1 in which the metal particles are silver and the magnetic material contains granules of samarium cobalt.

3. The conductive tape of claim 2 and including a volatile and organic solvent applied to said conductive and further coatings in which electrical continuity between the conductive coating and the further coating is enhanced by the application of said volatile and organic solvent to disperse metal particles from said coatings into contact with one another and activate the electrode.

4. The conductive tape of claim 3 in which the further coating is positioned on the opposite surface of the tape substrate from the conductive coating and includes plurality of spots to define a localized coating which adheres to the substrate through activation of the adhesive therein by a volatile and organic solvent.

5. The conductive tape of claim 4 and including at least one plate-like coupling device of a samarium cobalt material forming a permanent magnet and having an insulated wire connected thereto and positioned in contact with at least one of said localized coating spots.

6. The conductive tape of claim 5 and including a covering of non-allergenic tape coupling the plate-like coupling device of samarium cobalt into intimate contact with the localized spot of a conductive coating and magnetic material.

7. The conductive tape of claim 4 in which the conductive coating on said one surface of the substrate is divided into a plurality of isolated coatings separated by a general background of the conductive coating and in which the further coating mixture of conductive coating and magnetic material is positioned on the opposite surface of the substrate such that it defines localized spots opposite the localized coatings of the conductive coating separated from the background.

8. The conductive tape of claim 7 and including a plurality of plate magnets of magnetic material which are held in contact with the conductive magnetic coating spots on said opposite surface of the substrate, and insulating lead wires coupled to each of the magnets.

9. The conductive tape of claim 8 in which the plurality of magnets are formed of a samarium cobalt material and positioned in an overlay sheet to adhere thereto with the overlay sheet being held in contact with the substrate at the edges thereof.

10. The conductive tape of claim 1 in which the further coating is positioned on the tape substrate on the opposite surface from the conductive coating.

11. The conductive tape of claim 10 in which the further coating is positioned on the substrate to adhere to the substrate and the conductive coating through activation of the adhesive therein by the solvent, said further coating including a plurality of localized spots of magnetic and conductive particles.

* * * * *